United States Patent
Conlan et al.

(10) Patent No.: US 10,188,777 B2
(45) Date of Patent: *Jan. 29, 2019

(54) LIPOSUCTION DEVICE AND SYSTEM AND USE THEREOF

(71) Applicant: Aurastem LLC, Solana Beach, CA (US)

(72) Inventors: Bradford A. Conlan, Solano Beach, CA (US); Lucas Fornace, La Jolla, CA (US)

(73) Assignee: Aurastem LLC, Solana Beach, CA (US)

( * ) Notice: Subject to any disclaimer, the term of this patent is extended or adjusted under 35 U.S.C. 154(b) by 335 days.

This patent is subject to a terminal disclaimer.

(21) Appl. No.: 15/199,773

(22) Filed: Jun. 30, 2016

(65) Prior Publication Data

US 2017/0049942 A1   Feb. 23, 2017

Related U.S. Application Data

(60) Provisional application No. 62/207,746, filed on Aug. 20, 2015.

(51) Int. Cl.
*A61M 1/00* (2006.01)
*A61M 37/00* (2006.01)
(Continued)

(52) U.S. Cl.
CPC .......... *A61M 1/008* (2013.01); *A61M 1/0056* (2013.01); *A61M 37/0015* (2013.01);
(Continued)

(58) Field of Classification Search
CPC ............ A61M 2202/08; A61M 1/0056; A61M 1/007; A61M 1/008; A61M 1/0064; A61B 2017/00792
(Continued)

(56) References Cited

U.S. PATENT DOCUMENTS 5,002,538 A * 3/1991 Johnson ................ A61J 1/2096
604/240
5,744,360 A * 4/1998 Hu .......................... A61F 2/062
435/325

(Continued)

OTHER PUBLICATIONS

International Search Report for International Application No. PCT/US2016/040761, dated Sep. 12, 2016.
(Continued)

*Primary Examiner* — Susan S Su (74) *Attorney, Agent, or Firm* — Taylor English Duma LLP (57) ABSTRACT

Embodiments of the present invention disclose a device for removing adipose tissue with a needle(s), comprising a needle hub that comprises at least one needle that contains between 1-1000 holes around the circumference of the needle barrel which allows passage of adipose tissue and other lipoaspirate, and an adipose tissue collection and purification device comprising a plurality of self-contained syringes wherein each of the syringes comprises an inner syringe included within an outer syringe and wherein a filter is attached inside the outer syringe barrel, the filter having a mesh pore size between 30 micro meters and 1000 micro meters, the device being attached to a needle hub. The present invention further provides a system for closed adipose tissue harvesting, purification, and grafting, comprising an adipose tissue removal component, a collection and purification component, and a grafting component. Methods of using the devices or system are also disclosed.

32 Claims, 6 Drawing Sheets

(51) Int. Cl.
   *A61M 5/32* (2006.01)
   *A61B 17/00* (2006.01)
(52) U.S. Cl.
   CPC .... *A61B 2017/00792* (2013.01); *A61M 1/007* (2014.02); *A61M 5/3291* (2013.01); *A61M 2202/0007* (2013.01); *A61M 2202/0014* (2013.01); *A61M 2202/08* (2013.01); *A61M 2205/7563* (2013.01)
(58) Field of Classification Search
   USPC ........................................................ 604/542
   See application file for complete search history.

(56) References Cited

U.S. PATENT DOCUMENTS

| | | | |
|---|---|---|---|
| 5,817,050 A * | 10/1998 | Klein | A61M 1/008 604/35 |
| 5,911,700 A | 6/1999 | Mozsary et al. | |
| 5,968,008 A | 10/1999 | Grams | |
| 6,020,196 A | 2/2000 | Hu et al. | |
| 7,608,048 B2 | 10/2009 | Goldenberg | |
| 7,841,991 B2 | 11/2010 | Douglas et al. | |
| 7,914,504 B2 | 3/2011 | Klein | |
| 8,202,493 B2 | 6/2012 | Buss | |
| 8,489,172 B2 | 7/2013 | Gelbart et al. | |
| 8,652,123 B2 | 2/2014 | Gurtner et al. | |
| 2002/0151874 A1* | 10/2002 | Kolster | A61B 17/32002 604/542 |
| 2002/0169469 A1* | 11/2002 | Klein | A61B 17/320783 606/167 |
| 2003/0167053 A1* | 9/2003 | Taufig | A61M 1/0084 604/542 |
| 2004/0044331 A1* | 3/2004 | Klein | A61B 17/320783 604/542 |
| 2007/0010810 A1 | 1/2007 | Kochamba | |
| 2007/0055179 A1* | 3/2007 | Deem | A61K 41/0028 601/2 |
| 2007/0100277 A1* | 5/2007 | Shippert | A61M 1/0062 604/27 |
| 2007/0225686 A1* | 9/2007 | Shippert | A61M 1/0001 604/542 |
| 2007/0270710 A1 | 11/2007 | Frass et al. | |
| 2008/0154240 A1* | 6/2008 | Shippert | A61M 1/0001 604/542 |
| 2010/0057056 A1* | 3/2010 | Gurtner | A61B 17/320016 604/542 |
| 2010/0125240 A1* | 5/2010 | Spedden | A61B 17/0057 604/37 |
| 2010/0137841 A1* | 6/2010 | Khouri | A61M 1/0009 604/542 |
| 2010/0318070 A1* | 12/2010 | Mitra | A61B 5/14514 604/540 |
| 2012/0027804 A1* | 2/2012 | Odermatt | A61B 17/06166 424/400 |
| 2012/0165725 A1 | 6/2012 | Chomas et al. | |
| 2014/0155869 A1* | 6/2014 | Seare | A61M 1/0082 604/542 |
| 2015/0289858 A1* | 10/2015 | McGillicuddy | A61B 10/025 600/566 |
| 2015/0352266 A1* | 12/2015 | Gourlay | A61M 1/0001 604/542 |
| 2015/0374888 A1* | 12/2015 | Shippert | A61M 1/0001 604/542 |
| 2016/0058924 A1* | 3/2016 | Kim | A61M 1/008 604/542 |
| 2017/0203040 A1 | 7/2017 | Conlan | |
| 2017/0368226 A1* | 12/2017 | Pilkington | C12M 45/02 |
| 2018/0207331 A1 | 7/2018 | Conlan et al. | |

OTHER PUBLICATIONS

Written Opinion of the International Searching Authority for International Application No. PCT/US2016/040761, dated Sep. 12, 2016.
Conlan, Bradford A.; Non-Final Office Action for U.S. Appl. No. 15/422,304, filed Feb. 1, 2017, dated Sep. 27, 2018, 16 pgs.
Colan, Bradford A.; International Search Report and Written Opinion for PCT/US17/30247, filed Apr. 28, 2017, dated Jul. 19, 2017, 8 pgs.
Conlan, Bradford A.; International Preliminary Report on Patentability for PCT/US2016/040761, filed Jul. 1, 2016, dated Feb. 20, 2018, 9 pgs.

* cited by examiner

LIPOSUCTION DEVICE AND SYSTEM AND USE THEREOF

CROSS-REFERENCE TO RELATED APPLICATION

This application claims the benefit of U.S. provisional application Ser. No. 62/207,746, filed on Aug. 20, 2015, the teaching of which is incorporated herein by reference in its entirety.

FIELD OF THE INVENTION

The invention relates generally to biomedical sciences and technologies and particularly to tissue harvesting and tissue graft application devices and methods.

BACKGROUND OF THE INVENTION

The transfer of adipose tissue to various regions of the body is a relatively common cosmetic, therapeutic and structural procedure involving the harvest of adipose tissue from one location and re-implantation of the harvested and, oftentimes processed tissue, in another location (see Coleman 1995; and Coleman 2001). While being largely used for repair of small cosmetic defects such as facial folds, wrinkles, pock marks and divots; the transfer of adipose tissue has recently been used for cosmetic and/or therapeutic breast augmentation and reconstruction (Bircoll and Novack 1987; and Dixon 1988), and augmentation of the buttocks (Cardenas-Camarena, Lacouture et al. 1999; de Pedroza 2000; and Peren, Gomez et al. 2000).

In the past, adipose tissue grafts and methods of adipose tissue transfer have been plagued with difficulties and side effects including necrosis, absorption of the implant by the body, infection (Castello, Barros et al. 1999; Valdatta, Thione et al. 2001), calcifications and scarring (Huch, Kunzi et al. 1998), inconsistent engraftment, (Eremia and Newman 2000), lack of durability, and other problems arising from lack of neovascularization and necrosis of the transplanted tissue. One of the biggest challenges in adipose tissue transfer is absorption of the implant by the body and volume retention of adipose tissue grafts following transfer. When adipose tissue is harvested or washed, the space between individual pieces of harvested adipose tissue is filled by liquid (e.g., water, blood, tumescent solution, oil). When this tissue/fluid mixture is implanted into a recipient the liquid portion is rapidly absorbed by the body resulting in loss of volume. The process by which the amount of fluid is removed from the tissue/fluid mixture is frequently referred to as "drying the adipose tissue" or "dehydrating the adipose tissue". The content of red and white blood cells and the like within an adipose tissue graft can also significantly affect the volume of graft retained after graft transplantation, due to induction or exacerbation of an inflammatory response. Another aspect of tissue retention relates to the amount of lipid within the adipose tissue graft. It understood that the presence of free lipid (meaning lipids released from dead or damaged adipocytes; also referred to as oil) in adipose tissue grafts can result in induction or exacerbation of an inflammatory response with substantial phagocytic activity and consequent loss of graft volume.

It is also known that mixing unprocessed adipose tissue with a concentrated population of adipose-derived regenerative cells overcomes many of the problems associated with adipose tissue grafts and adipose tissue transfer, as described above. Specifically, supplementing unprocessed adipose tissue with concentrated populations of adipose-derived cells comprising adipose-derived stem cells increases the weight, vascularization, and retention of fat grafts. (See U.S. Pat. No. 7,390,484 and co-pending U.S. Patent Application Publication No. 2005/0025755, herein expressly incorporated by reference in their entireties). Adipose tissue fragments supplemented, or mixed, with a concentrated population of cells including adipose-derived stem cells exhibit improved neoangiogeneis and perfusion in grafts when compared to unsupplemented grafts of adipose tissue alone in animal models. Further, adipose tissue grafts supplemented with adipose-derived regenerative cells that comprise adipose derived stem cells show increased graft retention and weight over time, when compared to unsupplemented grafts. (See U.S. Patent Application Publication No. 2005/0025755). Further, the processing of adipose tissue in a closed, sterile fluid pathway greatly reduces the chance of infection. The improvement in autologous transfer of adipose tissue seen in the animal models described above has also been replicated in human clinical studies. Nevertheless, the isolation and purification of concentrated populations of adipose-derived regenerative cells comprising adipose-derived stem cells (ADSCs), usually involves a series of washing, digestion, filtration and/or centrifugation steps, which can reduce the yield of viable cells, require mechanical equipment and specialized clinicians, and/or can compromise the quality, appearance, longevity, hydration or efficacy of the graft.

Additionally, stresses could cause undesirable reactions to harvested adipose tissues. Such stresses include, for example, exposure to environmental pathogens, which are mentioned above, and prolonged post-harvest storage, etc. Therefore, there is a need for in-situ harvest, cleaning, and use of an adipose tissue graft for biomedical applications.

The need for additional approaches to prepare and optimize adipose tissue grafts and implants and to isolate and/or concentrate adipose-derived regenerative cells is manifest.

SUMMARY OF THE INVENTION

In one aspect of the present invention, it is provided a tissue removal device that allows for the removal of adipose tissue with a needle(s), comprising a needle hub that comprises at least one needle that contains between 1-1000 holes around the circumference of the needle barrel which allows passage of adipose tissue and other lipoaspirate.

In some embodiments of the invention device, optionally in combination with any or all the various embodiments described herein, the needle hub comprises a plurality of needles each of which contains between 1-1000 holes around the circumference of the needle barrel which allows passage of adipose tissue and other lipoaspirate.

In some embodiments of the invention device, optionally in combination with any or all the various embodiments described herein, the needle barrel is between 16 and 32 gauge in diameter.

In some embodiments of the invention device, optionally in combination with any or all the various embodiments described herein, the needle barrel is between 1 mm and 200 mm in length.

In some embodiments of the invention device, optionally in combination with any or all the various embodiments described herein, the holes contained around the circumference of the needle barrel have a geometry that allows for the cutting and removal of lipoaspirate as the device is pushed forward and backwards within the subcutaneous space.

In some embodiments of the invention device, optionally in combination with any or all the various embodiments described herein, the holes contained around the circumference of the needle barrel have a geometry that allows for the cutting and removal of lipoaspirate as the device is rotated within the subcutaneous space.

In some embodiments of the invention device, optionally in combination with any or all the various embodiments described herein, the device further comprises a guide that prevents the over insertion and under insertion and thus allows collection of subcutaneous adipose tissue at desired depth.

In some embodiments of the invention device, optionally in combination with any or all the various embodiments described herein, the guide is curved to allow puncture of the needle and forces the needle to remain in the subcutaneous layer of adipose tissue.

In some embodiments of the invention device, optionally in combination with any or all the various embodiments described herein, the guide further contains a mechanism that pinches the exterior of the skin and thus raises the subcutaneous fat layer to allow for insertion of the needle.

In some embodiments of the invention device, optionally in combination with any or all the various embodiments described herein, the guide further contains a vacuum mechanism capable of raising the subcutaneous fat layer to allow for insertion of the needle.

In some embodiments of the invention device, optionally in combination with any or all the various embodiments described herein, the device further comprises a blunt cannula where the cannula removably connects with the needle hub.

In some embodiments of the invention device, optionally in combination with any or all the various embodiments described herein, the device further comprises a blunt cannula where the cannula removably connects with the needle hub.

In another aspect of the present invention, it is provided an adipose tissue collection and purification device, comprising a plurality of self-contained syringes wherein each of the syringes comprises an inner syringe included within an outer syringe and wherein a filter is attached inside the outer syringe barrel, the filter having a mesh pore size between 30 micro meters and 1000 micro meters;

wherein the adipose tissue collection and purification device attaches to a needle hub; and wherein liposuctioned adipose tissue is collected and purified inside the plurality of syringes.

In some embodiments of the invention device, optionally in combination with any or all the various embodiments described herein, the inner syringe contained within the outer syringe is able to evacuate the waste product from lipoaspirated tissue into its barrel and remain contained within its barrel during the reinjection of remaining adipose contained within the filter of the outer syringe.

In some embodiments of the invention device, optionally in combination with any or all the various embodiments described herein, the inner syringe plunger contains a one-way valve that allows for the passage of lipoaspirate waste into its barrel but does not allow the lipoaspirate waste to re-enter the barrel of the outer syringe.

In some embodiments of the invention device, optionally in combination with any or all the various embodiments described herein, the filter is able to contain adipose tissue but is also collapsible thus allowing the adipose to exit the filter and be pushed outside the outer syringe.

In some embodiments of the invention device, optionally in combination with any or all the various embodiments described herein, the inner syringe contained within the outer syringe is able to evacuate the waste product from lipoaspirated tissue into a separate waste product chamber.

In some embodiments of the invention device, optionally in combination with any or all the various embodiments described herein, the filter is a multiple stage filter comprising a plurality of filters where a first stage of filtration uses a filter up to 1000 micro meters.

In a further aspect of the present invention, it is provided a system for closed adipose tissue harvesting, purification, and grafting, comprising an adipose tissue removal component, a collection and purification component, and a grafting component, wherein:

the adipose tissue removal component comprises a tissue removal device comprising a needle hub that comprises at least one needle that contains between 1-1000 holes around the circumference of the needle barrel which allows passage of adipose tissue and other lipoaspirate, the collection and purification component comprises an adipose tissue collection and purification device comprising a plurality of self-contained syringes wherein each of the syringes comprises an inner syringe included within an outer syringe and wherein a filter is attached inside the outer syringe barrel, the filter having a mesh pore size between 30 micro meters and 1000 micro meters;

wherein the adipose tissue collection and purification device attaches to a needle hub; and wherein liposuctioned adipose tissue is collected and purified inside the plurality of syringes.

In some embodiments of the invention system, optionally in combination with any or all the various embodiments described herein, the needle hub comprises a plurality of needles each of which contains between 1-1000 holes around the circumference of the needle barrel which allows passage of adipose tissue and other lipoaspirate.

In some embodiments of the invention system, optionally in combination with any or all the various embodiments described herein, the needle barrel is between 16 and 32 gauge in diameter.

In some embodiments of the invention system, optionally in combination with any or all the various embodiments described herein, the needle barrel is between 1 mm and 200 mm in length.

In some embodiments of the invention system, optionally in combination with any or all the various embodiments described herein, the holes contained around the circumference of the needle barrel have a geometry that allows for the cutting and removal of lipoaspirate as the device is pushed forward and backwards within the subcutaneous space.

In some embodiments of the invention system, optionally in combination with any or all the various embodiments described herein, the holes contained around the circumference of the needle barrel have a geometry that allows for the cutting and removal of lipoaspirate as the device is rotated within the subcutaneous space.

In some embodiments of the invention system, optionally in combination with any or all the various embodiments described herein, the tissue removal device further comprises a guide that prevents the over insertion and under insertion and thus allows collection of subcutaneous adipose tissue at desired depth.

In some embodiments of the invention system, optionally in combination with any or all the various embodiments described herein, the guide is curved to allow puncture of the needle and forces the needle to remain in the subcutaneous layer of adipose tissue.

In some embodiments of the invention system, optionally in combination with any or all the various embodiments described herein, the guide further contains a mechanism that pinches the exterior of the skin and thus raises the subcutaneous fat layer to allow for insertion of the needle.

In some embodiments of the invention system, optionally in combination with any or all the various embodiments described herein, the guide further contains a vacuum mechanism capable of raising the subcutaneous fat layer to allow for insertion of the needle.

In some embodiments of the invention system, optionally in combination with any or all the various embodiments described herein, the tissue removal device further comprises a blunt cannula where the cannula removably connects with the needle hub.

In some embodiments of the invention system, optionally in combination with any or all the various embodiments described herein, the tissue removal device further comprises a blunt cannula where the cannula removably connects with the needle hub.

In some embodiments of the invention system, optionally in combination with any or all the various embodiments described herein, the inner syringe contained within the outer syringe is able to evacuate the waste product from lipoaspirated tissue into its barrel and remain contained within its barrel during the reinjection of remaining adipose contained within the filter of the outer syringe.

In some embodiments of the invention system, optionally in combination with any or all the various embodiments described herein, the inner syringe plunger contains a one-way valve that allows for the passage of lipoaspirate waste into its barrel but does not allow the lipoaspirate waste to re-enter the barrel of the outer syringe.

In some embodiments of the invention system, optionally in combination with any or all the various embodiments described herein, the filter is able to contain adipose tissue but is also collapsible thus allowing the adipose to exit the filter and be pushed outside the outer syringe.

In some embodiments of the invention system, optionally in combination with any or all the various embodiments described herein, the inner syringe contained within the outer syringe is able to evacuate the waste product from lipoaspirated tissue into a separate waste product chamber.

In some embodiments of the invention system, optionally in combination with any or all the various embodiments described herein, the filter is a multiple stage filter comprising a plurality of filters where a first stage of filtration uses a filter up to 1000 micro meters.

In a further aspect of the present invention, it is provided a method of using the tissue removal device according to any of the various embodiments disclosed herein, the tissue collection and purification device according to any of the various embodiments disclosed herein, or the system according to any of the various embodiments disclosed herein. For the sake of concise description, the embodiments of the tissue removal device, the tissue collection and purification device, and the system described above are omitted but specifically incorporated herein by reference in their entirety.

In some embodiments of the invention method, optionally in combination with any or all the various embodiments described herein, the method is a biomedical application or a cosmetic application on a subject.

In some embodiments of the invention method, optionally in combination with any or all the various embodiments described herein, the subject is a human being.

DETAILED DESCRIPTION OF EMBODIMENTS OF THE INVENTION

Definitions

As used herein, the term "adipose tissue" is used interchangeably with the term "fat", the meaning of which is well known to a person of ordinary skill in the art.

As used herein, the term "adipose tissue removal" or "tissue removal" or "harvesting" or "liposuction" are used interchangeably to mean remove an amount of adipose tissue from a live subject such as a male or female patient.

As used herein, the term "collapsible" refers to the attribute of a material capable of collapsing under pressure or vacuum or capable of changing of shape or contour or of deformation in response to pressure change, and as such, in some embodiments, the term "collapsible" can mean deformable. An example of a material that is collapsible is a plastic or polymeric material forming a bag, e.g., a bag that is described in U.S. patent application Ser. No. 12/771,985, the teachings of which is incorporated herein by reference in its entirety.

As used herein, the term "filter" refers to a porous material having a size or size distribution useful for adipose tissue filtration. Some examples of filter useful for the present invention are described in U.S. patent application Ser. No. 12/771,985, the teachings of which is incorporated herein by reference in its entirety.

Micro Needles

In one aspect of the present invention, it is provided a tissue removal device that allows for the removal of adipose tissue with a needle(s), comprising a needle hub that comprises at least one needle that contains between 1-1000 holes around the circumference of the needle barrel which allows passage of adipose tissue and other lipoaspirate.

In some embodiments of the invention device, optionally in combination with any or all the various embodiments disclosed herein, the needle hub comprises a plurality of needles each of which contains between 1-1000 holes around the circumference of the needle barrel which allows passage of adipose tissue and other lipoaspirate.

In some embodiments of the invention device, optionally in combination with any or all the various embodiments disclosed herein, the needle barrel is between 16 and 32 gauge in diameter.

In some embodiments of the invention device, optionally in combination with any or all the various embodiments disclosed herein, the needle barrel is between 1 mm and 200 mm in length.

In some embodiments of the invention device, optionally in combination with any or all the various embodiments disclosed herein, the holes contained around the circumference of the needle barrel have a geometry that allows for the cutting and removal of lipoaspirate as the device is pushed forward and backwards within the subcutaneous space. In some embodiments, the holes contained around the circumference of the needle barrel have a geometry that allows for the cutting and removal of lipoaspirate as the device is rotated within the subcutaneous space.

In some embodiments of the invention device, optionally in combination with any or all the various embodiments disclosed herein, the device further comprising a guide that prevents the over insertion and under insertion and thus allows collection of subcutaneous adipose tissue at desired depth.

In some embodiments of the invention device, optionally in combination with any or all the various embodiments disclosed herein, the guide is curved to allow puncture of the needle and forces the needle to remain in the subcutaneous layer of adipose tissue.

In some embodiments of the invention device, optionally in combination with any or all the various embodiments disclosed herein, the guide further contains a mechanism that pinches the exterior of the skin and thus raises the subcutaneous fat layer to allow for insertion of the needle.

Adipose Tissue Collection and Purification

In a further aspect of the present invention, it is provided an adipose tissue collection and purification device comprising a plurality of self-contained syringes wherein each of the syringes comprises an inner syringe included within an outer syringe and wherein a filter is attached inside the outer syringe barrel, the filter having a mesh pore size between 30 micro meters and 1000 micro meters;

wherein the adipose tissue collection and purification device attaches to a needle hub; and wherein liposuctioned adipose tissue is collected and purified inside the plurality of syringes.

In some embodiments of the invention device, optionally in combination with any or all the various embodiments disclosed herein, the inner syringe contained within the outer syringe is able to evacuate the waste product from lipoaspirated tissue into its barrel and remain contained within its barrel during the reinjection of remaining adipose contained within the filter of the outer syringe.

In some embodiments of the invention device, optionally in combination with any or all the various embodiments disclosed herein, the inner syringe plunger contains a one-way valve that allows for the passage of lipoaspirate waste into its barrel but does not allow the lipoaspirate waste to re-enter the barrel of the outer syringe.

In some embodiments of the invention device, optionally in combination with any or all the various embodiments disclosed herein, the filter is able to contain adipose tissue but is also collapsible thus allowing the adipose to exit the filter and be pushed outside the outer syringe.

Figure 8A:
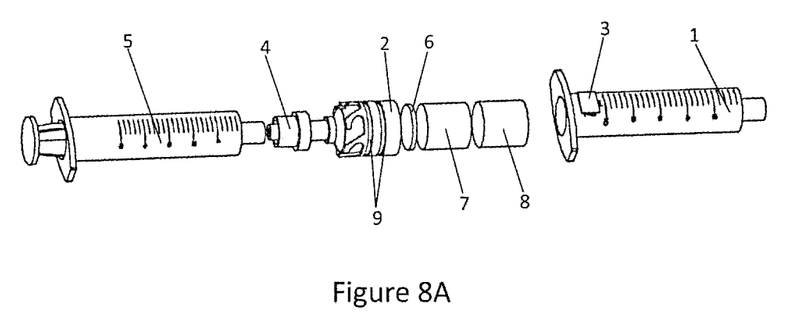
FIGS. 8A and 8B show an embodiment of an invention device.
Figure 8B:
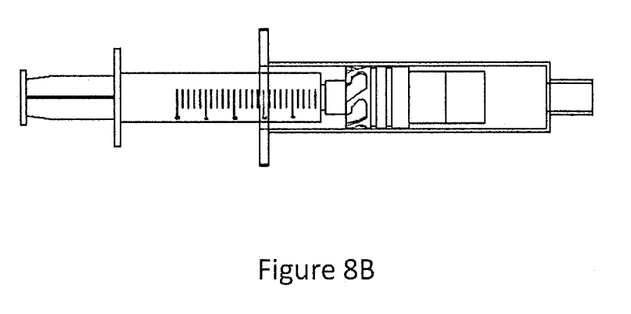

An embodiment of the invention device is described in FIGS. 8A and 8B (PUREGRAFT 10 SYRINGE ASSEMBLY). Referring to FIG. 8A, element 1 is an outer syringe barrel, 2 is a piston, 3 is a locking pin, 4 is a valve (e.g, a check valve), 5 is an inner syringe, which is also referred as a female syringe, 6 is a filter component, which can be, for example, a polyester mesh (e.g., 73 micron with 40% open area), 7 is an additional filter component, which can be, for example, 20 PPI polyester foam, 8 is a further additional filter component, which can be, for example, 45 PPI polyester foam, 6-8 comprising a multiple stage depth filter element of the invention device, and 9 is an O-ring, which can have a size of [2 mm×11 mm ID], made of silicone, e.g. FIG. 8B shows the assembly of the invention device of FIG. 8A.

Figure 9:
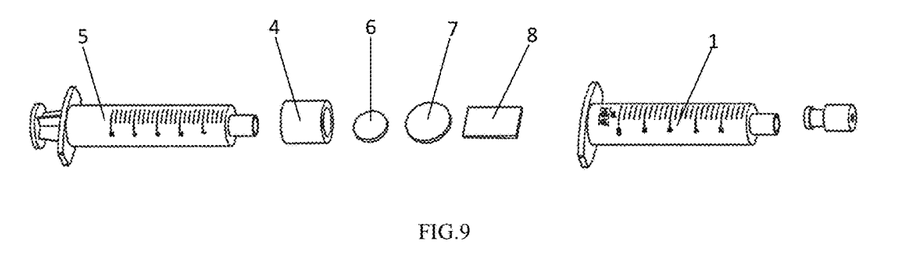
FIG. 9 shows an embodiment of an invention device having an outer syringe and an inner syringe.

Another embodiment of the invention device is described in FIG. 9. Referring to FIG. 9, the invention device embodiment includes 1, an outer syringe barrel, 4, a valve, 5, an inner syringe, 6, a filter component (a mesh), 7, an additional filter component (a foam), and a further additional filter component, 8 (a 73 micron filter disk). In one embodiment, the specifications of the elements of the device in FIG. 9 are the same as the corresponding elements of the device of FIG. 8A.

Adipose Tissue Harvesting, Collection and Purification, and Application

In a further aspect of the present invention, it is provided a system for closed adipose tissue harvesting, purification, and grafting, comprising an adipose tissue removal component, a collection and purification component, and a grafting component, wherein:

the adipose tissue removal component comprises a tissue removal device of the various embodiments disclosed herein, and the collection and purification component comprises an adipose tissue collection and purification device of the various embodiments disclosed herein.

Figure 10:
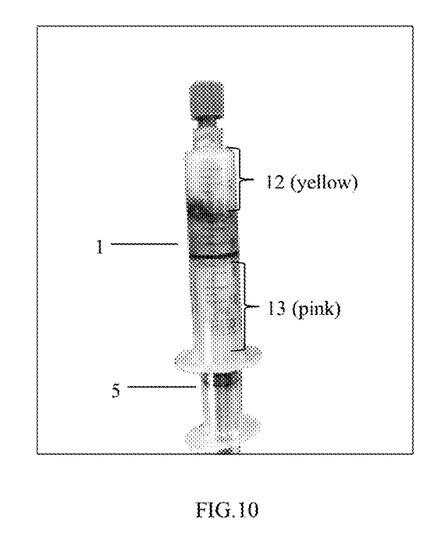
FIG. 10 shows an embodiment of an invention device where a volume of cleaned fat tissue (yellow) is included in the larger outer syringe and a volume of waste in included in the inner syringe (pink).

FIG. 10 describes an assembled invention device embodiment of FIG. 9 in use of tissue harvesting. As shown in FIG. 10, a volume of tissue (12) was collected and cleaned in the outer syringe 1, and the waste (13) was collected in the inner syringe 5.

Method of Use

In a further aspect of the present invention, it is provided a method of using the device of invention, the adipose tissue collection and purification device of invention and/or the system of invention. In some embodiments, the use includes biomedical and cosmetic applications on a subject. Cosmetic applications can be, for example, organ reshaping or augmentation. Biomedical applications can be, for example, tissue grafting, and cell therapy or tissue regenerative therapies.

EXAMPLES

Example 1

Figure 1:
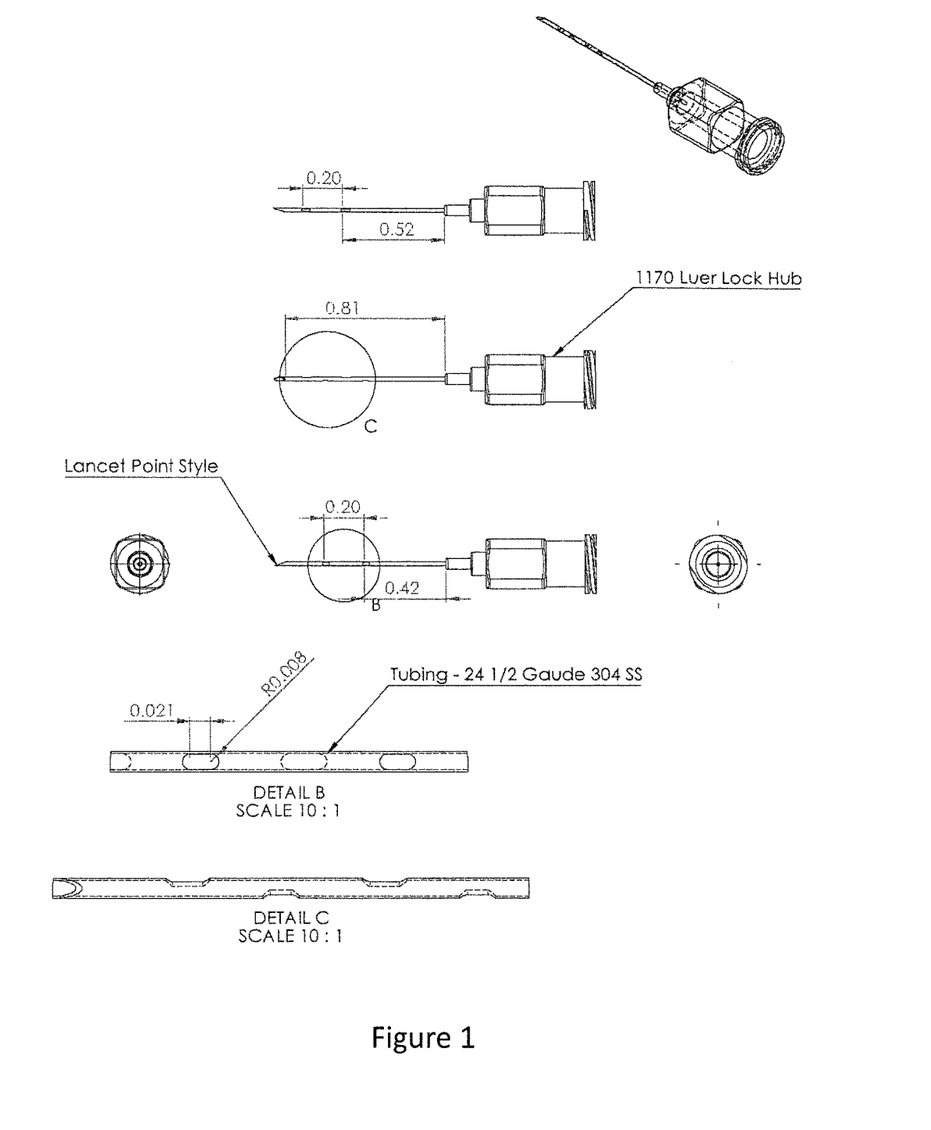
FIG. 1 illustrates embodiments of a needle of the present invention.
Figure 2A:
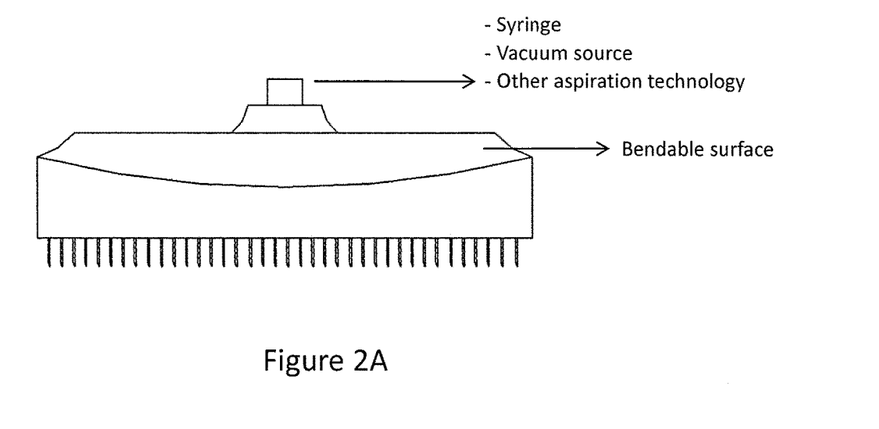
FIG. 2 illustrates an embodiment of the invention wherein a needle hub comprises one or a plurality of needles (1-1000 needles) having a bendable/depressible surface to allow up and down agitation and a method of using the device.
Figure 2B:
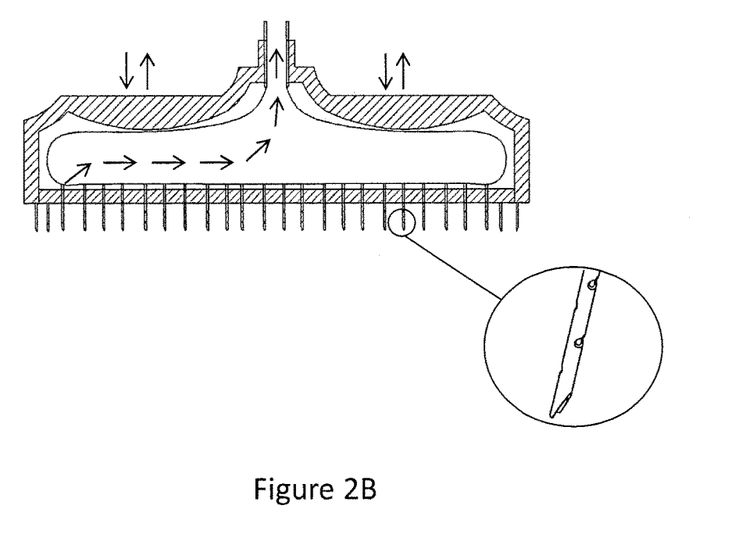
Figure 2C:
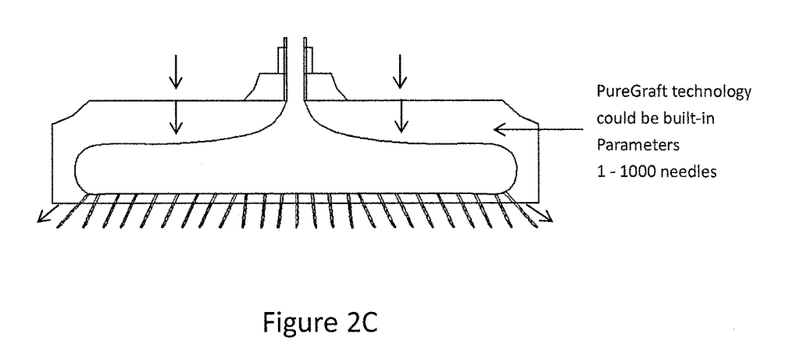
Figure 2D:
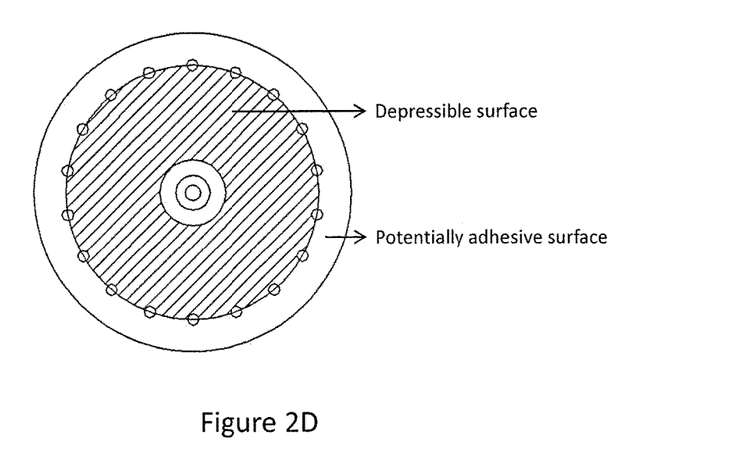

Designs of exemplary needles of invention are shown in FIG. 1.

Example 2

FIG. 2 illustrates an embodiment of the invention wherein a needle hub comprises one or a plurality of needles (1-1000 needles) having a bendable/depressible surface to allow up and down agitation and a method of using the device (Example 2). In some embodiments, the bendable/depressible surface can be an adhesive surface.

A method of using the device of invention of FIG. 2 can include the following steps:
a) attach the device of FIG. 2 to a patient;
b) insert infiltration fluid and wait for a period of time, e.g., 10 minutes;
c) agitate by pressing the bendable surface multiple times; and
d) suction up lipoaspirate.

Example 3. Studies Report on Micro Needle Liposuction

To develop a novel and commercially viable method of harvesting small volumes (up to 50 cc of adipose tissue, there are three design challenges that must be overcome for this project to be successful. They are as follows:
1. Design of a micro cannula that does not require incisions to be used, as most cannulas are at least 0.1" to 0.3" in diameter. This allows one to use micro needle array to harvest the tissue without any incisions or tissue harvesting can be achieved and "doesn't require incisions to be made. In some embodiments, the device of invention may include a combination needle plus blunt cannula, where the former makes the incision and the latter cuts the tissue. This can be made automated and in one step, hidden from the user.
2. Integrated method to capture the adipose tissue from the lipoaspirate, as the PureGraft™ bag does now. It allowed the harvested tissue to be washed of any contaminates before the transfer step for re-injection.
3. Developing an aseptic method to transfer the adipose tissue to small syringe for implantation. In some embodiments, the syringe itself can be the delivery/implantation vehicle. Alternatively, if desired, the tissue can be transferred from one syringe to another (presumably smaller) syringe in an aseptic fashion.

Studies on animal models were performed and showed that 1) and 2) requirements were met. The third requirement can be solved using mechanical design of off-the-shelf aseptic ports to transfer the tissue.

Figure 3:
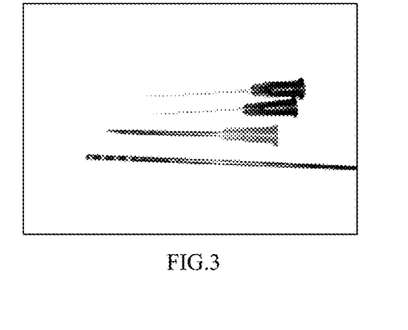
FIGS. 3-7 shows various designs of embodiments of invention tissue removal device.

The first design requirement focuses on the cannula design. There was a lot of development work done, to determine the correct size and configuration that would work for this application. We know that small needles, 28 gauge and up can be insert in the skin little to no pain (28 ga. is currently used for insulin injects, OD is 0.014" and ID is 0.009"). For comparison, the smallest cannula used in liposuction procedures has a combined suction opening area of 0.006 in$^2$ and we can duplicate that using an array of five of the custom thin wall 25.5 ga. to 28 ga. needles. For our testing we have been testing standard 16 ga. and 22 ga. needles, as they are easier for me to make custom ground side port openings in my shop. In testing both the 16 ga. and 22 ga. needle with animal fat, (Pork Bellies) we were able to demonstrate the needles could remove adipose tissue without clogging (See FIG. 3). We are working is Vita Needles to make custom cannula needles of the correct size and configuration.

Figure 4:
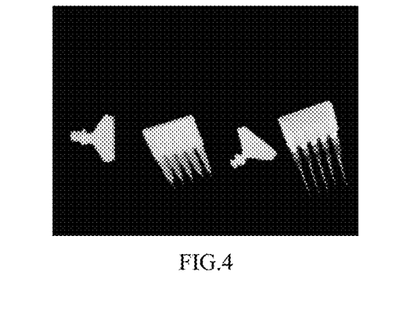
Figure 5A:
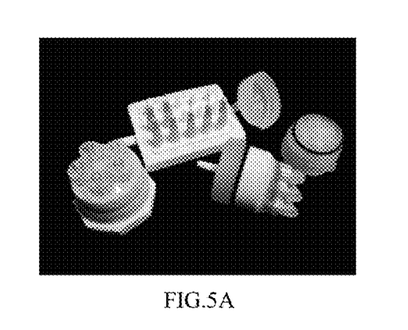
Figure 5B:
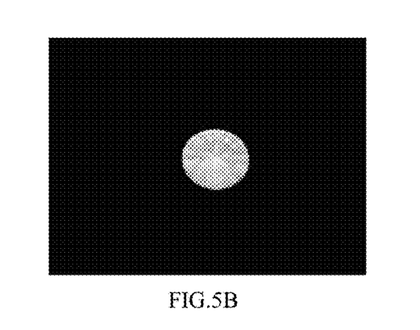

The second design requirement is the ability to capture the adipose tissue and rinse it after it has been harvested. We are currently testing many configuration and material to capture the adipose tissue from the lipoaspirate. Using 3D printer, we have been able to prototype many differing designs and configurations to test to collect the adipose tissue (See FIG. 4). We have evaluated differing designs, finding that we can use many different shapes and configurations. Another key to the design is to create fine grid membrane that the tissue will attach to and not be removed with the liposuction or rinsing. We have found one membrane that works well in collecting the adipose tissue. (See FIG. 5)

Example 4. Tissue Harvesting Via Micro Needle Liposuction

A closed adipose tissue harvesting and cleaning procedure was successfully carried out using an embodiment invention device of FIG. 9. As shown in FIG. 10, a volume of tissue (12) was collected and cleaned in the outer syringe 1, and the waste (13) was collected in the inner syringe 5. The cleaned adipose tissue 12 is ready for use.

Figure 6:
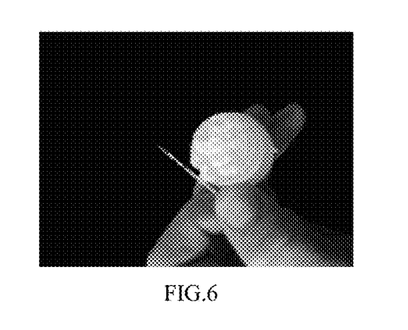
Figure 7:
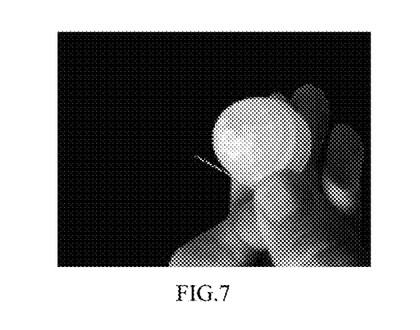

We have successfully combined these requirements into one device that has been used to harvest animal fat. We tested both needle cannulas with animal fat to show that tissue could be collected without clogging of the cannulas. The first test was with the 16 ga needle and the tissue separation device and was able to collect 1-2 grams in just a few minutes. (See FIG. 6) Using animal fat (Pork Bellies) is considered a worst case test for us, in that we cannot really introduce tumescent fluid, and the tissue is at room temperature. But that we were able to collect measurable amount of tissue in a short time was significant. Our initial goal is to be able to collect 5 to 10 grams of adipose tissue in less than 10 minutes. We tested using a 22 ga. needle modified with 4 side ports. Again, we were able to collect measurable amount of animal tissue in a short period of time. (See FIG. 7) Comparing the two images, you can see that the 22 ga. needle is much smaller, but able to get about the same amount of adipose tissue.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The teachings of the references, including patents and patent related documents, cited herein are incorporated herein in their entirety to the extent not inconsistent with the teachings herein.

We claim:
1. A device that allows for the removal of adipose tissue with a needle(s), comprising a needle hub that comprises at least one needle having a needle barrel that contains between 1-1000 holes around the circumference of the needle barrel which allows passage of adipose tissue and other lipoaspirate and a guide that prevents the over insertion and under insertion of the needle and thus allows collection of subcutaneous adipose tissue at desired depth,
wherein the guide is curved to allow the needle to puncture skin and the needle is adapted to remain in the subcutaneous layer of adipose tissue.
2. The device of claim 1, wherein the needle hub comprises a plurality of needles each of which contains between 1-1000 holes around the circumference of the needle barrel which allows passage of adipose tissue and other lipoaspirate.
3. The device of claim 1, wherein the needle barrel is between 16 and 32 gauge in diameter.
4. The device of claim 1, wherein the needle barrel is between 1 mm and 200 mm in length.
5. The device of claim 1, wherein the holes contained around the circumference of the needle barrel have a geom- etry that allows for the cutting and removal of lipoaspirate as the device is pushed forward and backwards within a subcutaneous space.

6. The device of claim 1, wherein the holes contained around the circumference of the needle barrel have a geometry that allows for the cutting and removal of lipoaspirate as the device is rotated within a subcutaneous space.

7. The device of claim 1, wherein the guide further contains a mechanism that pinches the exterior of the skin and thus raises the subcutaneous fat layer to allow for insertion of the needle.

8. The device of claim 1, wherein the guide further contains a vacuum mechanism capable of raising the subcutaneous adipose tissue layer to allow for insertion of the needle.

9. An adipose tissue collection and purification device comprising a plurality of self contained syringes wherein each of the syringes comprises an inner syringe included within an outer syringe and wherein a filter is attached inside a barrel of the outer syringe, the filter having a mesh pore size between 30 micro meters and 1000 micro meters;
wherein the adipose tissue collection and purification device attaches to a needle hub; and
wherein liposuctioned adipose tissue is collected and purified inside the plurality of syringes.

10. The adipose tissue collection and purification device of claim 9, wherein the inner syringe contained within the outer syringe is adapted to evacuate waste product from liposuctioned adipose tissue into its barrel the inner syringe also adapted to contain within its barrel said waste product during the reinjection of remaining adipose tissue contained within the filter inside the outer syringe.

11. The adipose tissue collection and purification device of claim 9, wherein the inner syringe comprising a plunger containing a one-way valve that allows for the passage of waste product from liposuctioned adipose tissue into a barrel of the inner syringe, said one-way valve prevents said waste product from reentering the outer syringe barrel.

12. The adipose tissue collection and purification device of claim 9, wherein the filter is capable of containing the liposuctioned adipose tissue therein, the filter is also collapsible to allow the liposuctioned adipose tissue to exit the filter and be pushed outside the outer syringe.

13. The adipose tissue collection and purification device of claim 9, wherein the inner syringe contained within the outer syringe is capable of evacuating waste product from liposuctioned adipose tissue into a separate waste product chamber.

14. The adipose tissue collection and purification device of claim 9, wherein the filter is a multiple stage filter comprising a plurality of filters wherein a first filter of said plurality of filters has a mesh pore size of up to 1000 micro meters.

15. A system for closed adipose tissue harvesting, purification, and grafting, comprising an adipose tissue removal component, a collection and purification component, and a grafting component,
wherein:
the adipose tissue removal component comprises a tissue removal device comprising a needle hub that comprises at least one needle that contains between 1-1000 holes around the circumference of a barrel of the needle which allows passage of adipose tissue and other lipoaspirate,
the collection and purification component comprises an adipose tissue collection and purification device comprising a plurality of self contained syringes wherein each of the syringes comprises an inner syringe included within an outer syringe and wherein a filter is attached inside the outer syringe barrel, the filter having a mesh pore size between 30 micro meters and 1000 micro meters;
wherein the adipose tissue collection and purification device attaches to a needle hub;
and wherein liposuctioned adipose tissue is collected and purified inside the plurality of syringes.

16. The system according to claim 15, wherein the needle hub comprises a plurality of needles each of which contains between 1-1000 holes around the circumference of a barrel of the needle which allows passage of adipose tissue and other lipoaspirate.

17. The system according to claim 15, wherein the needle barrel is between 16 and 32 gauge in diameter.

18. The system according to claim 15, wherein the needle barrel is between 1 mm and 200 mm in length.

19. The system according to claim 15, wherein the holes contained around the circumference of the needle barrel have a geometry that allows for the cutting and removal of lipoaspirate as the device is pushed forward and backwards within the subcutaneous space.

20. The system according to claim 15, wherein the holes contained around the circumference of the needle barrel have a geometry that allows for the cutting and removal of lipoaspirate as the device is rotated within the subcutaneous space.

21. The system according to claim 15, wherein the tissue removal device further comprises a guide that prevents the over insertion and under insertion of the needle and thus allows collection of subcutaneous adipose tissue at desired depth.

22. The system according to claim 21, wherein the guide is curved to allow the needle to puncture skin and the needle is adapted to remain in a subcutaneous layer of adipose tissue.

23. The system according to claim 21, wherein the guide further contains a mechanism configured to pinch the exterior of a skin and to raise the subcutaneous adipose tissue to allow for insertion of the needle.

24. The system according to claim 21, wherein the guide further contains a vacuum mechanism capable of raising the subcutaneous adipose tissue to allow for insertion of the needle.

25. The system according to claim 15, wherein the inner syringe contained within the outer syringe is adapted to evacuate waste product from liposuctioned adipose tissue into its barrel the inner syringe also adapted to contain within its barrel said waste product during the reinjection of remaining adipose tissue contained within the filter inside the outer syringe.

26. The system according to claim 15, wherein the inner syringe comprising a plunger containing a one-way valve that allows for the passage of waste product from liposuctioned adipose tissue into a barrel of the inner syringe, said one-way valve prevents said waste product from reentering the outer syringe barrel.

27. The system according to claim 15, wherein the filter is capable of containing the liposuctioned adipose tissue therein, the filter is also collapsible to allow the liposuctioned adipose tissue to exit the filter and be pushed outside the outer syringe.

28. The system according to claim 15, wherein the inner syringe contained within the outer syringe is capable of evacuating waste product from liposuctioned adipose tissue into a separate waste product chamber.

29. The system according to claim 15, the filter is a multiple stage filter comprising a plurality of filters where a first stage of filtration uses a filter up to 1000 micro meters.

30. A method, comprising either steps a) and b) as a first option or step c) as a second option:
- a) removing a tissue from a subject using a tissue removal device comprising a needle hub that comprises at least one needle that contains between 1-1000 holes around the circumference of a barrel of the needle which allows passage of adipose tissue and other lipoaspirate,
- b) collecting and purifying a tissue using an adipose tissue collection and purification device comprising a plurality of self contained syringes wherein each of the syringes comprises an inner syringe included within a barrel of an outer syringe and wherein a filter is attached inside the barrel of the outer syringe, the filter having a mesh pore size between 30 micro meters and 1000 micro meters;

wherein the adipose tissue collection and purification device attaches to a needle hub; and wherein liposuctioned adipose tissue is collected and purified inside the plurality of syringes, or
- c) harvesting, purifying, and grafting a tissue using a system comprising an adipose tissue removal component, a collection and purification component, and a grafting component, wherein the adipose tissue removal component comprises a tissue removal device as defined in step a), and wherein the collection and purification component comprises an adipose tissue collection and purification device as defined in step b).

31. The method of claim 30, wherein the method is for biomedical application or cosmetic application on the subject.

32. The method of claim 31, wherein the subject is a human being.

\* \* \* \* \*